US007550721B2

(12) United States Patent
Chen et al.

(10) Patent No.: US 7,550,721 B2

(45) Date of Patent: Jun. 23, 2009

(54) METHOD AND APPARATUS FOR DEPOSITING SAMPLES ON A TARGET SURFACE

(75) Inventors: Vincent C. Chen, Winnipeg (CA); Helene Perreault, Winnipeg (CA)

(73) Assignee: University of Manitoba, Winnipeg, Manitoba ( * ) Notice: Subject to any disclaimer, the term of this patent is extended or adjusted under 35 U.S.C. 154(b) by 581 days.

(21) Appl. No.: 11/427,592

(22) Filed: Jun. 29, 2006

(65) Prior Publication Data

US 2007/0023681 A1 Feb. 1, 2007

Related U.S. Application Data

(60) Provisional application No. 60/694,685, filed on Jun. 29, 2005.

(51) Int. Cl.
*H01J 49/00* (2006.01)

(52) U.S. Cl. ....................... 250/288; 250/281; 250/287; 422/63; 422/100

(58) Field of Classification Search ......... 250/281–300; 422/63, 100
See application file for complete search history.

(56) References Cited

U.S. PATENT DOCUMENTS 5,037,611 A * 8/1991 Ledford, Jr. .................. 422/63
6,674,070 B2 1/2004 Karger et al.
6,680,477 B2 * 1/2004 Beck et al. .................. 250/288
6,727,494 B2 * 4/2004 Lin ............................ 250/282
6,806,465 B2 * 10/2004 Anderson et al. ........... 250/287
6,825,463 B2 11/2004 Karger et al.
6,878,343 B2 4/2005 Sklar et al.
7,232,688 B2 * 6/2007 Little et al. ................ 436/173

OTHER PUBLICATIONS

Chen, Vincent C. et al, "Device for the Reversed-Phase Separation and On-Target Deposition of Peptides Incorporating a Hydrophobic Sample Barrier for Matrix-Assisted Laser Desorption/Ionization Mass Spectrometry", Analytical Chemistry, vol. 76, No. 4, Feb. 15, 2004.

* cited by examiner

*Primary Examiner*—David A Vanore
*Assistant Examiner*—Andrew Smyth
(74) *Attorney, Agent, or Firm*—Philip C. Mendes da Costa; Bereskin & Parr LLP

(57) ABSTRACT

There is provided a sample deposition device for depositing samples on a target surface such as MALDI target surfaces for use in mass spectrometry analysis. The device comprises a vacuum chamber, a sealable opening communicating with the vacuum chamber, a sample inlet and a sample outlet. The sample outlet is located in the vacuum chamber which is sealed by contact with the target surface. The sample is drawn through the sample inlet and deposited on the surface by the action of the vacuum.

23 Claims, 8 Drawing Sheets

FLOW
ELECTRICAL JUNCTION POINT
BUFFER pH TO CHARGE ANALYTE +VE
CAN USE VACUUM TO DEPOSIT SAMPLE
MALDI TARGET

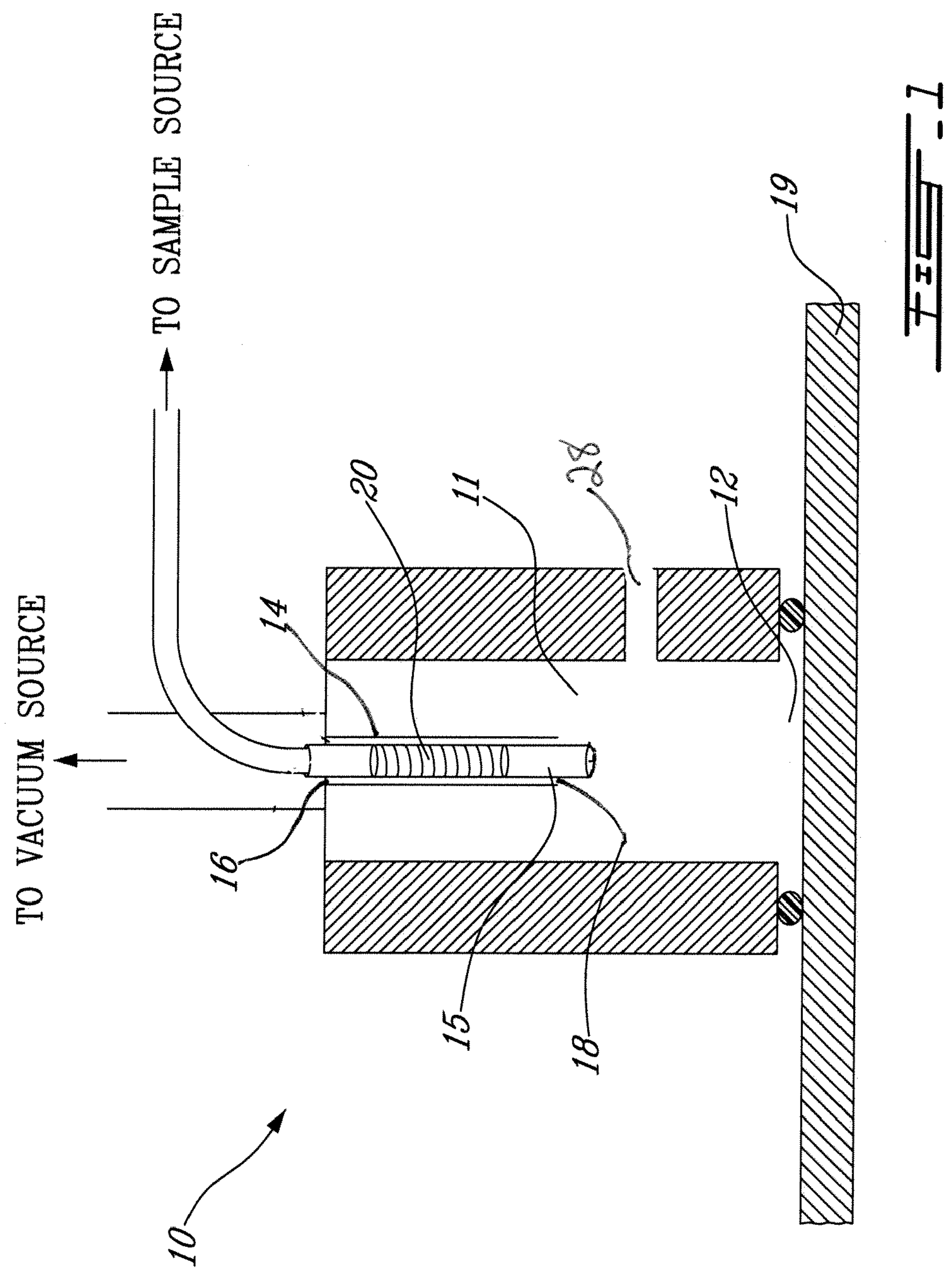
TO SAMPLE SOURCE
TO VACUUM SOURCE
10
11
12
14
15
16
18
19
20
28

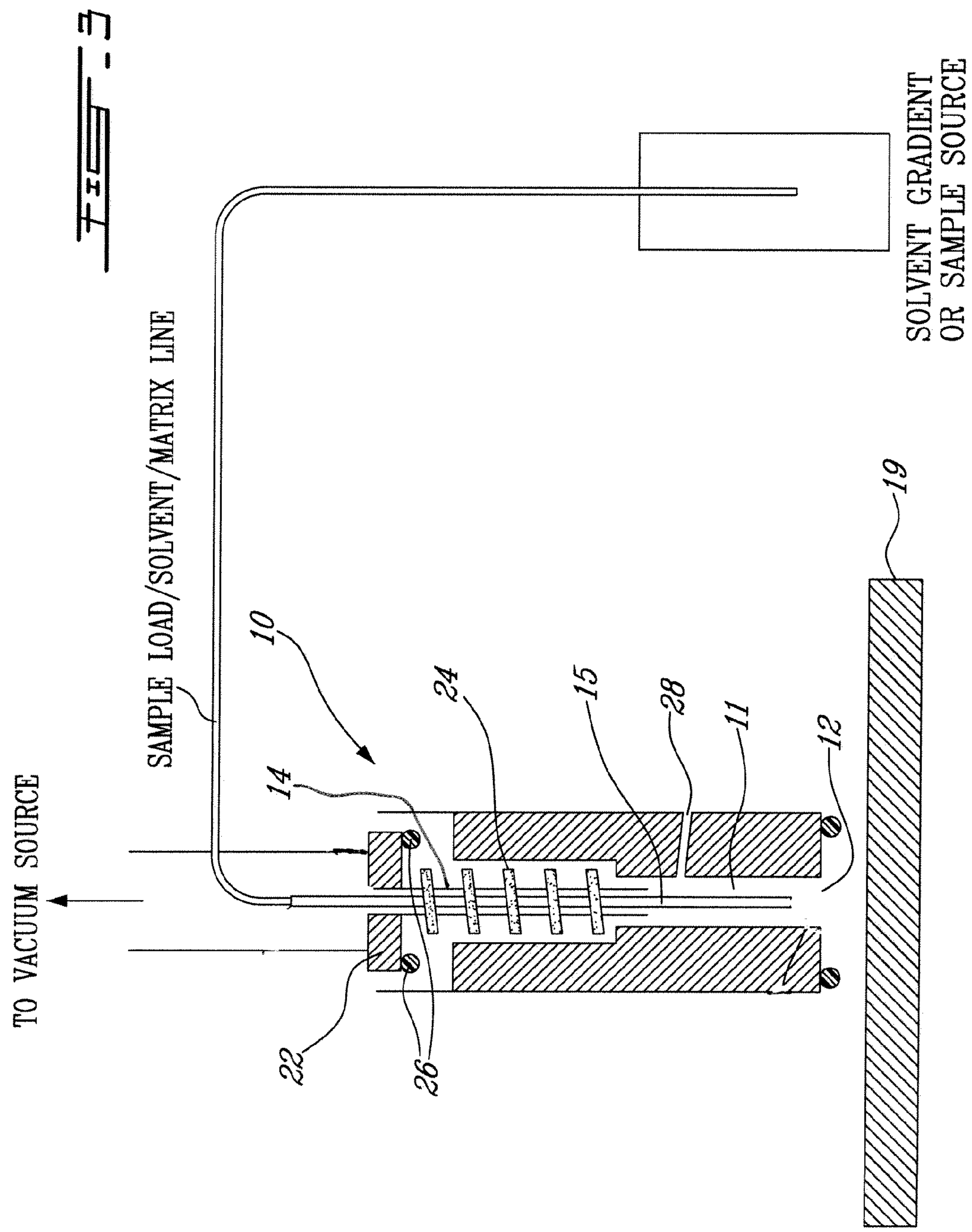
TO VACUUM SOURCE
SAMPLE LOAD/SOLVENT/MATRIX LINE
SOLVENT GRADIENT
OR SAMPLE SOURCE
10
14
24
15
28
11
12
19
22
26

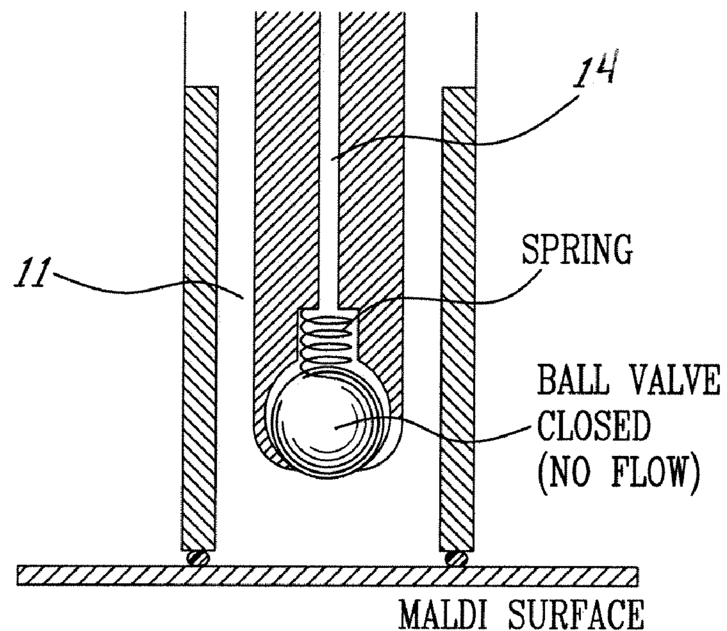
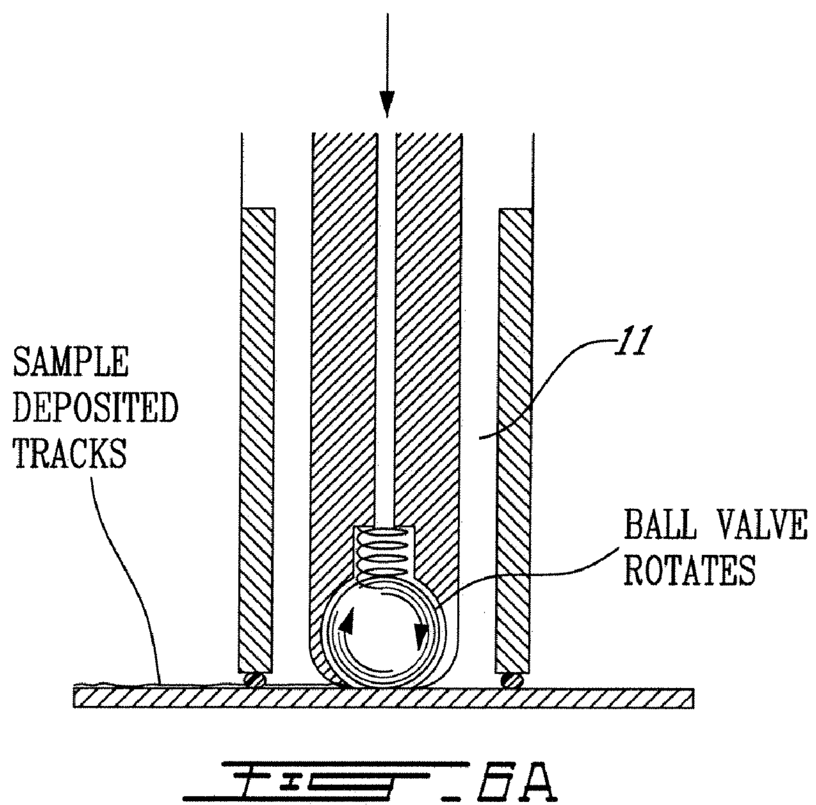
FIG. 6A

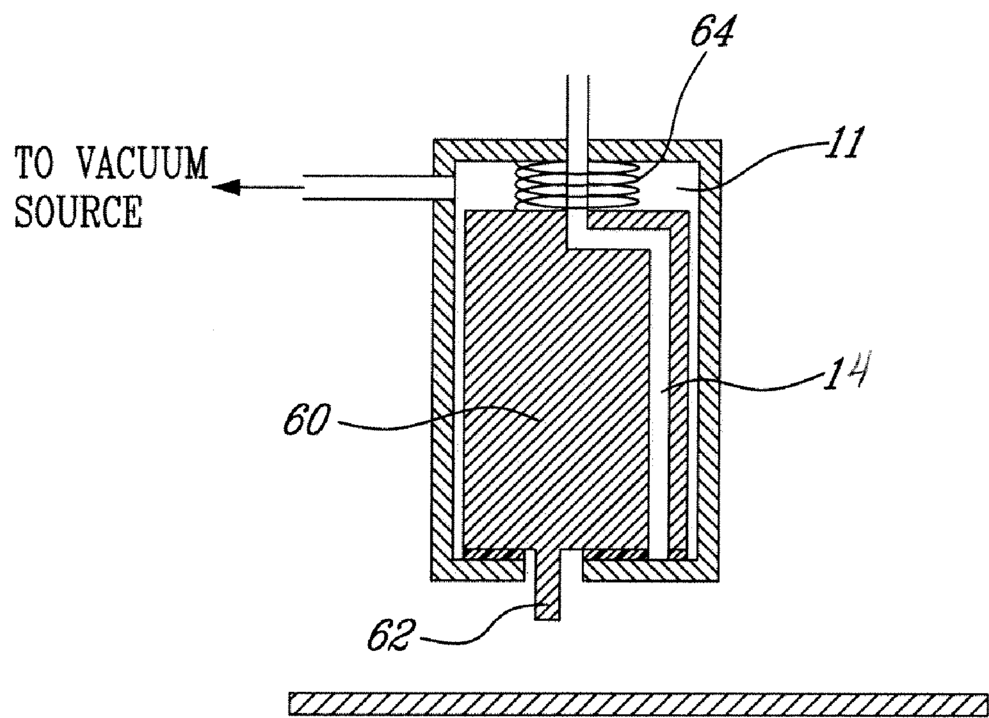
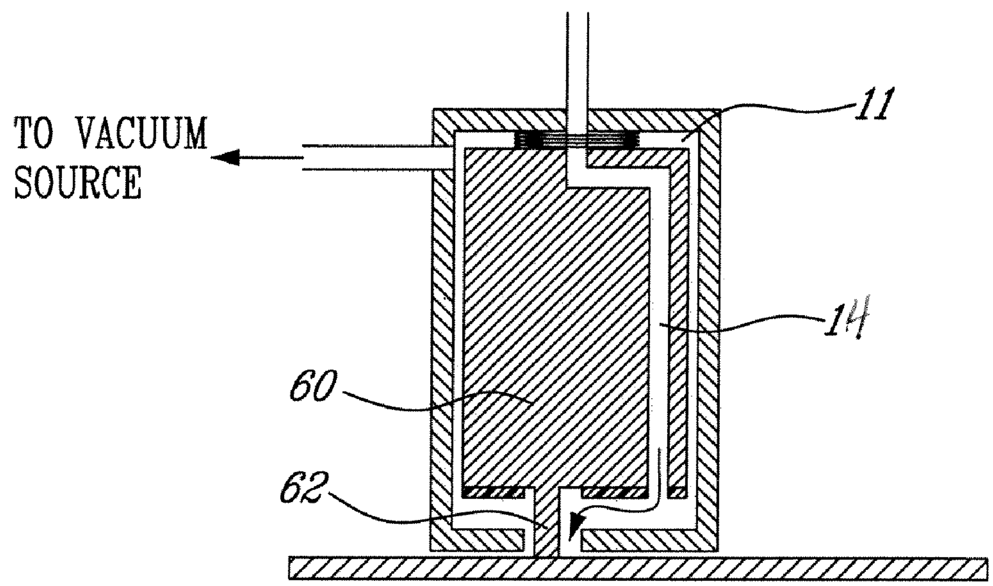
FIG. 6B

METHOD AND APPARATUS FOR DEPOSITING SAMPLES ON A TARGET SURFACE

CROSS-REFERENCE TO RELATED APPLICATION

This patent application claims priority on U.S. provisional application No. 60/694,685 entitled "METHOD AND APPARATUS FOR DEPOSITING SAMPLES ON A TARGET SURFACE" filed on Jun. 29, 2005.

FIELD OF THE INVENTION

The invention relates to the field of macromolecules separating device and more specifically to the field of macromolecules separating device for mass spectrometry analysis.

BACKGROUND OF THE INVENTION

Mass spectrometry has become a major analytical tool in proteomic and biological research in general. Most protein identification strategies involving MS analyze proteolytic peptides (e.g. tryptic digests for mass fingerprinting in combination with tandem MS to confirm amino acid sequence and the presence of various posttranslational modifications. In most proteome studies, proteins are separated on electrophoretic gels and in-gel digestion extracts are subjected to MS analysis. Although matrix assisted laser desorption/ionization (MALDI) is very effective for screening high abundance proteins in complex samples, lower abundance peptides often remain undetected. Suppression effects are a common problem arising from the presence of multiple analytes competing for protons during the ionization process. Various separation methods have been coupled to mass spectrometry to improve identification of macrolecules. However, efficient coupling to MALDI have been more difficult. High throughput MALDI requires deposition of multiple sample drops on a MALDI target plate. Chen et al. (analytical Chemistry vol 76, No 4, 2004) have proposed a method for separating molecules within samples and depositing drops of the eluent on a MALDI target surface by using negative pressure. However, their apparatus comprises a cumbersome vacuum chamber box in which the MALDI target and the separation device are inserted. Drop deposition is made difficult by the limited number of degrees of freedom for displacing the tip of the separation device relative to the target. A similar arrangement with a subatmospheric deposition chamber is described in Karger et al. (U.S. Pat. Nos. 6,674,070 and 6,825,463) Accordingly better coupling of separating/drop deposition device and targets are needed.

SUMMARY OF THE INVENTION

In one embodiment of the invention there is provided a sample deposition device comprising a housing which in turn comprises a vacuum chamber, a sealable opening communicating with the vacuum chamber, a vacuum inlet, a sample inlet and a sample outlet, the sample outlet located in the vacuum chamber, and wherein the sealable opening is sealed by a target surface when the housing is placed in sample deposition position on the target surface. A sample is drawn through the sample outlet and deposited on the target surface when a vacuum is applied in the vacuum chamber.

In a further embodiment of the invention a separating chamber is coupled to the sample inlet and the sample outlet thereby providing a mean for separating/purifying samples comprising different types of molecules such as a protein samples for example.

In another aspect of the invention there is provided a method for depositing drops of a sample on a target surface said method comprising: providing a target surface, providing a vacuum activated sample depositing device wherein the target surface is a sealing member of the device, applying a vacuum to the device to draw a sample towards the target surface and effect deposition of one or more drops and releasing the vacuum.

By using the target surface as a sealing member, the vacuum activated drop deposition device of the present invention provides a simplified set up for separating and depositing sample drops in rapid and flexible manner.

BRIEF DESCRIPTION OF THE DRAWINGS

Further features and advantages of the present invention will become apparent from the following detailed description, taken in combination with the appended drawings, in which:

FIG. 1 is a cross-sectional view of an embodiment of the device of the present invention;

FIG. 3 is cross-sectional view of an embodiment of the device shown with a removable lid;

FIG. 6A is an embodiment of the invention using a ball valve; and

FIG. 6B is an embodiment of the invention using a piston.

DETAILED DESCRIPTION OF THE INVENTION

Figure 2A:
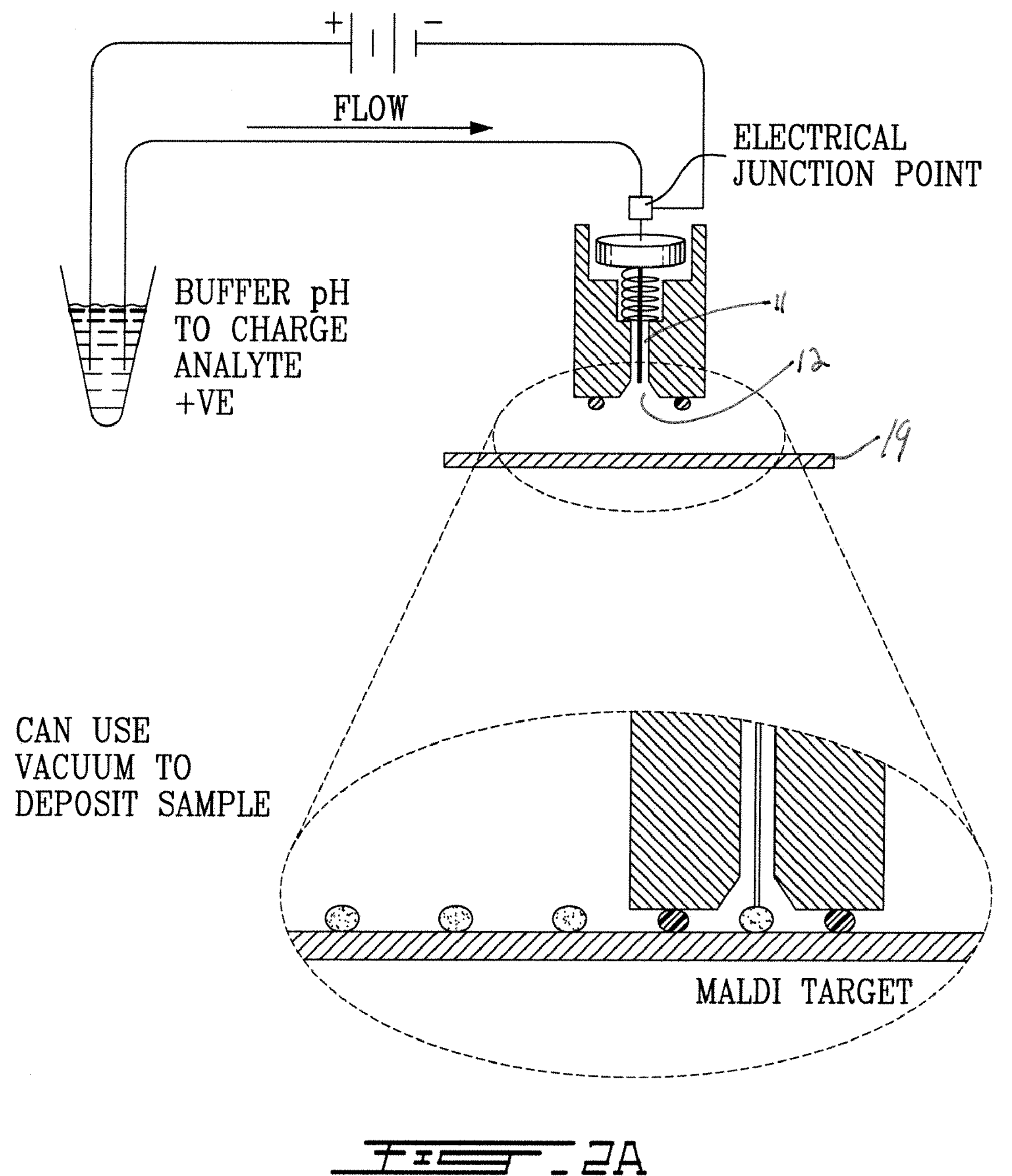
FIG. 2A shows an embodiment of the invention in which capillary electrophoresis is used for the separation of molecules.

A vacuum activated sample depositing/separating device is provided for deposition of samples on a target surface such as a MALDI target surface for mass spectral analysis of the sample.

An embodiment of the sample depositing device of the present invention is shown in FIG. 1. The device comprises a housing 10 which in turn comprises a vacuum chamber 11, a sealable opening 12 communicating with the vacuum chamber, a sample channel 14 comprising a sample inlet 16 connected to a sample source and a sample outlet 18 located inside the vacuum chamber.

The sample can be circulated directly in the sample channel 14 but, alternatively, it is also possible to insert a sample duct 15 within the sample channel or directly within the vacuum chamber. The sample duct may be adapted to help control the flow of the sample depending for example on the viscosity of the sample. Thus the size, shape and material of the duct may be chosen as function of the sample to be deposited. Furthermore the duct can be removed to be cleaned or replaced. When a sample duct is used, the sample channel may serve as a vacuum inlet which connects the vacuum chamber to a vacuum source. However, it will be appreciated that the vacuum inlet can be located anywhere along the vacuum chamber.

In operation, that is, when a drop of sample is deposited, the housing is placed on the target surface 19 at a desired location such that the target surface serves as a sealing member for the sealable opening 12. When a vacuum is applied within the vacuum chamber, the sample is drawn through the sample outlet and deposited on the surface. The use of the target surface as a sealing member for the vacuum chamber advantageously allows the housing to be easily displaced over the target surface.

In a preferred embodiment a separation chamber 20 is positioned between and connected with sample inlet 16 and sample outlet 18 such that when a vacuum is applied the sample is drawn into the separation chamber through sample inlet 16 and ultimately exiting the separation chamber through sample outlet 18 to be deposited on target surface 19. The separation chamber may be part of sample duct 15. The separation chamber 20 may be made in whole or in part of any suitable material including but not limited to bendable material that may facilitate the positioning of the separating chamber within the housing.

In one embodiment the sample comprises a mixture of protein of interest that are preferably separated prior to be deposited on a target surface in preparation for mass spectrometry analysis. The separation of the molecules can be achieved by various means such as chromatography and electrophoresis. Non-limiting examples include capillary electrophoresis, hydrophobic chromatography, ion exchange chromatography, affinity chromatography, size exclusion chromatography, chromatofocusing, capillary electrochromatography, solid phase extraction and the like. Monolithic columns, which are made of a porous network scaffold, can advantageously be used since they exhibit lower packing density when compared with traditional chromatographic material, which uses microbeads, and therefore allow the use of lower vacuum (closer to atmospheric pressure). Thus the separation chamber 20 may consist of a chromatographic column or capillary.

Figure 2B:
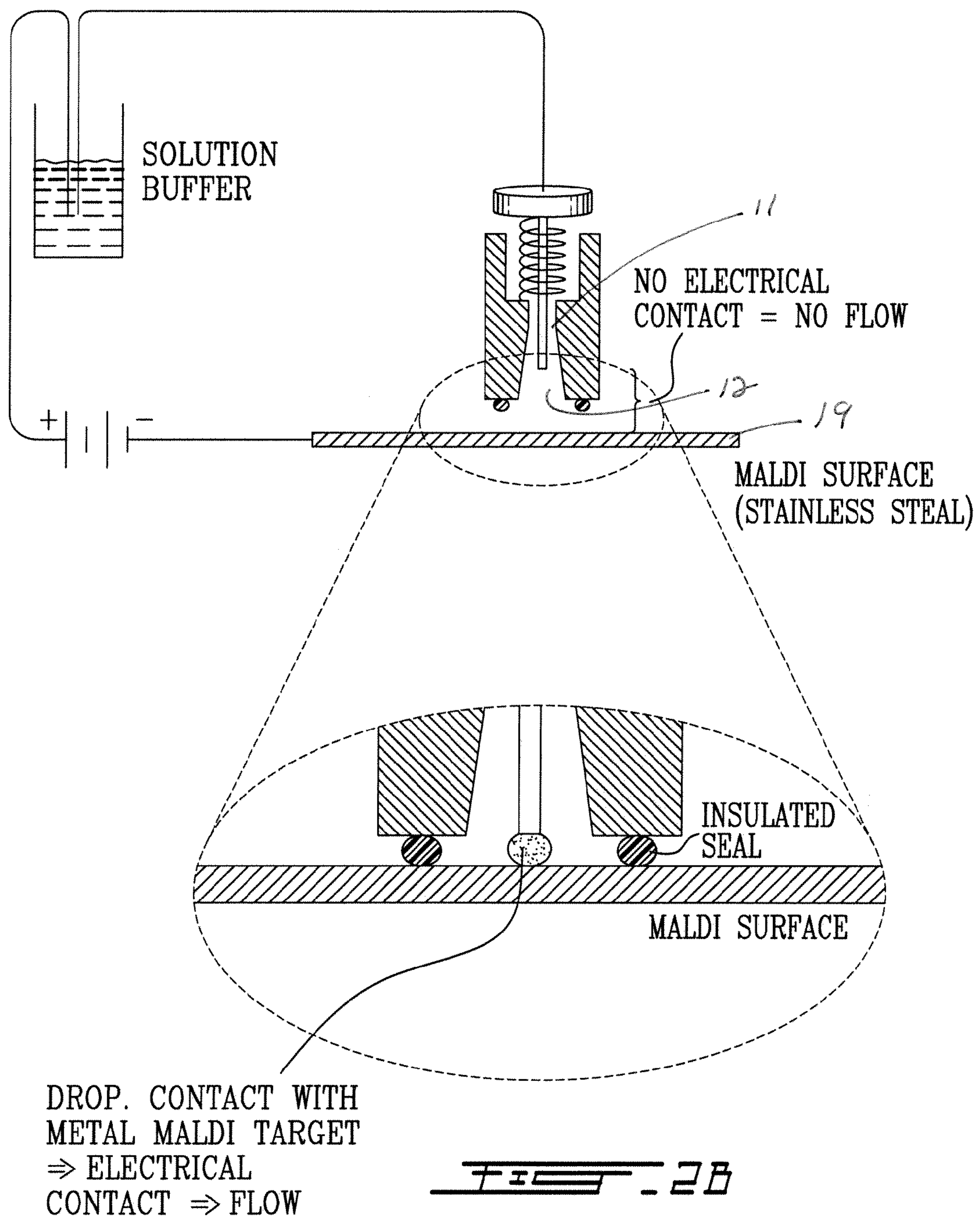
FIG. 2B shows an embodiment of the invention in which capillary electrophoresis is used for the separation of molecules wherein the target surface is part of the electric circuitry.

When using capillary electrophoresis the separation may be achieved by applying a voltage at the sample source and the separation chamber (see FIG. 2A). Once the analytes (macromolecules) are separated into "zones" the deposition of the drops may be effected by applying the vacuum. However in one particularly advantageous realization of the invention, the separation voltage may be applied between the sample and the target surface thereby producing a flow and separation within the separation chamber (see FIG. 2B). The current is established when the drop makes contact with the target surface. In this last embodiment a vacuum may or may not be applied.

In one embodiment, the vacuum chamber can be sealed by introducing separation chamber 20 directly into the vacuum chamber or through sample channel 14 and with a sealing member such as a rubber "O" ring. In another embodiment, and referring to FIG. 3, a removable lid 22 comprising sample channel 14 can be used. A biasing member 24, such as a spring, when no vacuum is being applied, can maintain the lid in an open position. Sealing members 26 are preferably coupled to the lid to provide a tight seal between the lid and the housing.

The separating chamber can be removeably attached to the lid or allowed to slide through sample inlet. In the first case the position of the separating chamber relative to the target surface, and therefore of sample outlet 18 is controlled by displacement of the lid. For example, if a biasing member is maintaining the lid open, a force can be applied on the lid which will cause the vacuum chamber to be sealed and bring the sample outlet in proximity to the target surface for sample deposition. In the second case the position of the separating chamber can be controlled manually by a user or automatically by using motorized robot for example by sliding the separating chamber in the sample inlet to a desired position inside the vacuum chamber.

While the connection to the vacuum source is shown in FIGS. 1 and 3 as being made through sample channel 14, it will be appreciated that it can be located at any other place along the vacuum chamber. It will also be appreciated that in the latter embodiment, a proper sealing member should be provided between the separation chamber and/or sample duct and sample chamber 14. For example, in the case where the separation chamber is a chromatographic column, the column could be inserted in a rubber "O" ring. Other types of sealing members are well known in the art.

The deposition of a sample drop may be effected as follows: the housing is brought in juxtaposition of the target surface by placing sealable opening 12 on the target surface, at a position where a drop is to be deposited, thereby effecting the sealing of this end of the vacuum chamber. The vacuum is then applied to draw the sample through the sample inlet and sample outlet and effect deposition of a sample drop. The cycle is completed by releasing the vacuum and displacing the device to the next drop deposition position. While the release of the vacuum can be effected by pulling the housing away from the target surface, in a preferred embodiment a valve or opening 28 connected to the vacuum chamber is provided for controlled release of the vacuum so as to avoid disturbing the deposited drop. If a separating chamber is being used, the application of a vacuum creates a flow of the sample through the separation chamber thereby effecting separation of the molecules within the sample.

The vacuum intensity and its duration can be adjusted such as to effect the deposition of a desired volume of sample and to control the speed at which the sample is carried through the separation chamber. The volume deposited at each spot on the surface may also be controlled by changing the distance between sample outlet 18 and the target surface.

Figure 4A:
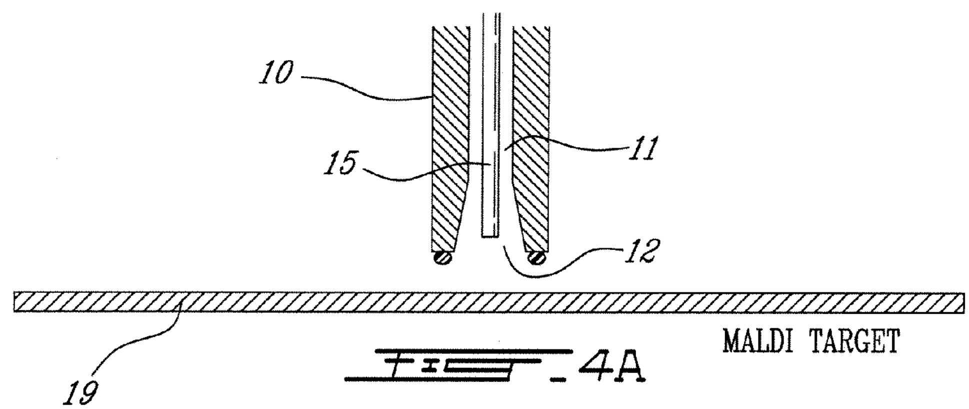
FIG. 4 is a cross-sectional view of an embodiment of the device showing housings of different dimensions occupying increasingly larger surface areas on the target surface.
Figure 4B:
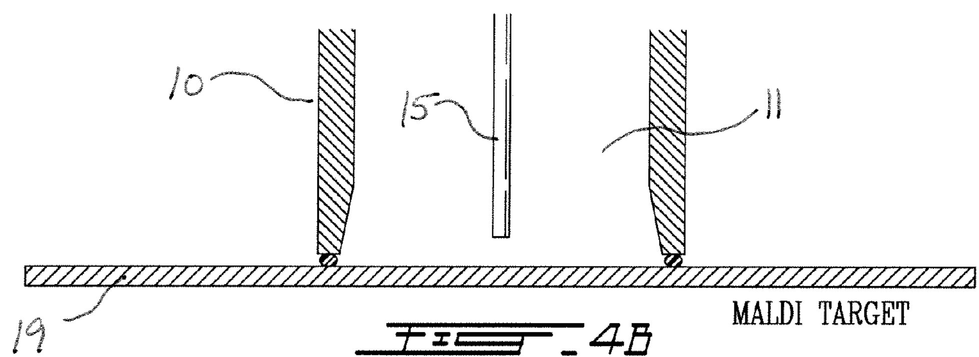
Figure 4C:
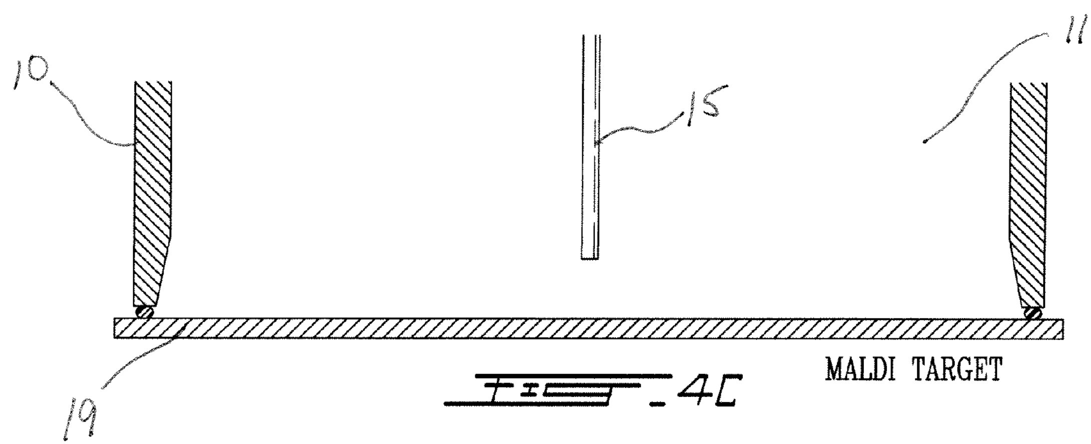

The surface occupied by the housing at the point of contact with the target surface can be tailored to the need of a particular application. In one aspect, the contact surface area may be dictated by the desired spacing between drops. However, the surface area occupied by the housing on the surface is only limited by the surface area of the target surface (see FIG. 4). In one embodiment, the surface area occupied by the housing on the target surface is sufficiently large so that the volume of the vacuum chamber may allow the displacement of the separation chamber to apply more than one drop at different positions while the housing remains stationary on the target surface.

Figure 5:
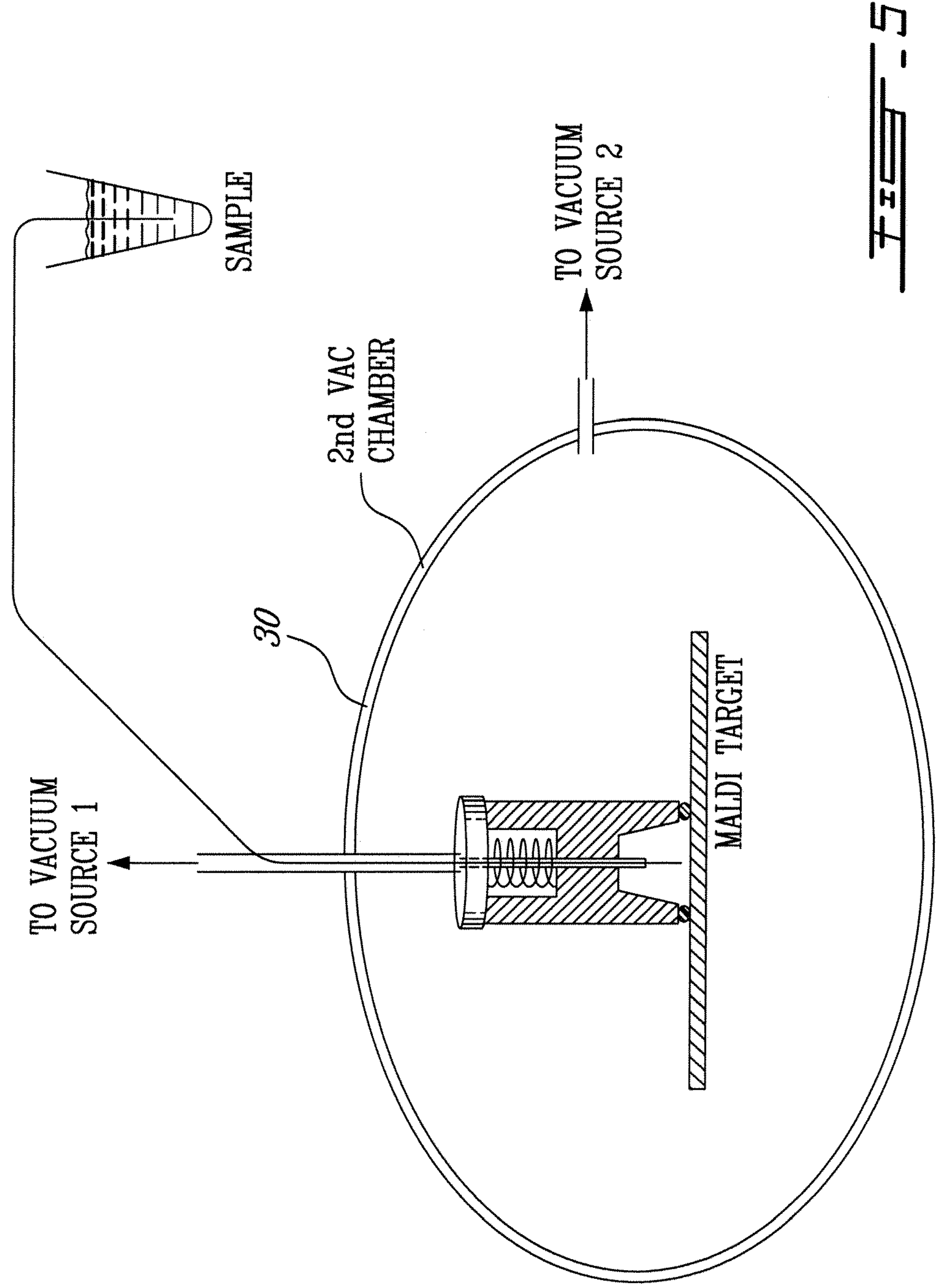
FIG. 5 is a perspective view of an embodiment of the device in which a second vacuum chamber is shown.

It is desirable to release the vacuum after drop(s) deposition in a controlled manner so as to avoid disturbing the drop(s). This can be achieved by controlling the release of the vacuum with valves. In an embodiment of the invention this can also be achieved by providing a second vacuum chamber 30 (FIG. 5) in which the target surface and the housing can be placed. The vacuum in the second vacuum chamber is maintained at a pressure slightly higher than the pressure within the vacuum chamber of the device but lower than the atmospheric pressure. This arrangement allows the release of the pressure within the vacuum chamber of the device with minimal disturbance of the drop. The pressure in the second vacuum chamber can be adjusted to produce a sample flow albeit at a lower rate than the flow generated by the vacuum in the vacuum chamber 11 or alternatively it can be adjusted to be insufficient to generate solvent flow.

Other embodiments of the invention are depicted in FIGS. 6A and 6B. In FIG. 6A the sample channel 14 within vacuum chamber 11 has a ball valve to control the delivery of the sample on the target surface. When the device is in the delivery position i.e. against the target surface the ball is displaced upwards and the sample can flow on the surface. When the device is not in the delivery position a biasing means such as a spring, pushes the ball against the opening and prevents the flow of the sample. This embodiment advantageously allows the sample to be spread on the surface or to be deposited as discrete spots.

FIG. 6B exemplifies yet another embodiment wherein the actuation of the sample flow is effected by a piston 60 having a piston contact bar 61. When the device is contacting the target surface the piston is displaced upwards and the bottom of the housing comes in contact with the target surface. The upward displacement of the piston enables the vacuum source and creates a sample flow for deposition on the surface. When the device is not in a delivery position the piston is biased against the bottom of the housing by biasing means 64 prevent the vacuum from creating a sample flow. It will be appreciated that when the device is in a second vacuum chamber, the bottom of the housing need not come in contact with the target surface since the vacuum is external to the housing.

While the device can easily be hand held and manipulated by a user, it will be appreciated that the various steps in the deposition of a sample drop can be performed mechanically by a computer-controlled robot. In particular, mechanical manipulation is advantageous in the embodiment where a second vacuum chamber is used and whereby manipulation of the device is performed inside the second vacuum chamber by mechanical means. It will further be appreciated that not only the displacement of the housing over the target surface may be automated but any aspect of the apparatus that is amenable to mechanical control. For example, displacement of the separating chamber within the vacuum chamber, particularly in the embodiment in which the vacuum chamber is large enough to allow deposition of several drops at different positions on the target surface, control of vacuum release, vertical adjustment of the sample outlet and the like. Furthermore, positioning of the housing, and therefore the drops, on the target surface may also be accomplished by displacing the surface while maintaining the housing stationary. Displacement of both the housing and the target surface is also possible.

In one embodiment of the invention the deposition device can be coupled to an automated liquid handier (liquid handling robot) such as to provide motion control of the device as well as regulation of the solvent/sample liquid flow into sample duct. It will be appreciated that in the case where a liquid handler is used, the liquid flow is controlled by the negative pressure within the device and the liquid pressure exerted by the pump of the liquid handler.

In a preferred embodiment the deposition device of the present invention is used to separate and deposit macromolecules on the surface of a MALDI target. By macromolecules it is meant proteins, peptides, oligonucleotides and the likes. MALDI target plates are well known in the art and may consist but are not limited to a stainless steel plate such as the Bruker Daltonics 384 target.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A sample deposition device comprising:

a housing comprising:

i) a vacuum chamber;

ii) a sealable opening communicating with said vacuum chamber;

iii) a vacuum inlet;

iv) a sample channel having a sample inlet and a sample outlet, said sample outlet located in said vacuum chamber; and wherein said sealable opening is sealed by a target surface when said housing is placed in sample deposition position on said target surface and wherein a sample is drawn through said sample outlet and deposited on said target surface when a vacuum is applied in said vacuum chamber.

2. The sample deposition device as claimed in claim 1 further comprising a sample duct adapted to fit in said sample channel.

3. The sample deposition device as claimed in claim 1 further comprising a sample separating chamber positioned between said sample inlet and said sample outlet such that said sample is drawn through said separation chamber when a vacuum is applied.

4. The sample deposition device as claimed in claim 3 wherein said separating chamber is comprised within a sample duct.

5. The sample deposition device as claimed in claim 1 further comprising a removable lid wherein said lid is sealably connected to said housing when closed.

6. The sample deposition device as claimed in claim 5 wherein said sample inlet is comprised in said lid.

7. The sample deposition device as claimed in claim 5 further comprising a biasing member for biasing said lid in an open position.

8. The sample deposition device as claimed in claim 7 wherein said biasing means is a spring.

9. The sample deposition device as claimed in claim 5 wherein said separating chamber is removably attached to said lid whereby said sample outlet is brought in sample deposition position when said lid is closed.

10. The sample deposition device as claimed in claim 3 wherein said separating chamber is a chromatographic column.

11. The sample deposition device as claimed in claim 10 wherein said chromatographic column comprises said sample inlet and outlet.

12. The sample deposition device as claimed in claim 11 wherein said column can be displaced laterally within said vacuum chamber such as to enable deposition of two or more sample drops at two or more positions on said target surface while said housing is maintained stationary.

13. The sample deposition device as claimed in claim 1 wherein said target surface is a MALDI target.

14. The sample deposition device as claimed in claim 1 further comprising a vacuum outlet for controllably releasing said vacuum.

15. The sample deposition device as claimed in claim 14 wherein said target surface and said vacuum outlet are comprised within a second vacuum chamber having an adjustable internal pressure below atmospheric pressure and above a pressure in said first vacuum chamber.

16. The sample deposition device as claimed in claim 1 wherein said sample comprises proteins of interest.

17. A sample deposition system comprising a sample deposition device having a housing comprising:

i) a vacuum chamber;

ii) a sealable opening communicating with said vacuum chamber;

iii) a vacuum inlet;

iv) a sample inlet and a sample outlet, said sample outlet located in said vacuum chamber; and wherein said sealable opening is sealed by a target surface when said housing is placed in sample deposition position on said target surface and wherein a sample is drawn through said sample outlet and deposited on said target surface when a vacuum is applied in said vacuum chamber; and an automated liquid handler wherein said automated liquid handler is operationally coupled to said sample deposition device.

18. A method for depositing drops of a sample on a target surface said method comprising:

a) providing a target surface b) providing a vacuum activated sample depositing device wherein said target surface comprises a sealing member of said device;

c) applying a vacuum to said device to draw said sample towards said target surface and effect deposition of one or more drop; and d) releasing said vacuum.

19. The method as claimed in claim 18 further comprising a step of separating components of said sample while said sample is being drawn by said vacuum.

20. The method as claimed in claim 19 wherein said sample comprises proteins of interest.

21. The method as claimed in claim 20 wherein said target surface is a MALDI target.

22. The method as claimed in claim 18 wherein said sealing member occupies a part of said target surface when said housing is in a sample deposition position.

23. The method as claimed in claim 18 wherein said sealing member occupies substantially all of said target surface when said housing is in a sample deposition position and wherein said sample outlet is displaced within the vacuum chamber to deposit sample at two or more positions on said target surface.

* * * * *